US005744692A

United States Patent [19]
Cervone et al.

[11] Patent Number: 5,744,692
[45] Date of Patent: Apr. 28, 1998

[54] NUCLEOTIDE SEQUENCES CODING AN ENDOPOLYGALACTURONASE INHIBITOR

[75] Inventors: Felice Cervone; Giulia De Lorenzo; Giovanni Salvi, all of Rome, Italy; Peter Albersheim, Athens, Ga.; Alan Darvill, Athens, Ga.; Carl Bergmann, Athens, Ga.

[73] Assignee: University of Georgia Research Foundation, Inc., Athens, Ga.

[21] Appl. No.: 244,646

[22] PCT Filed: Dec. 4, 1992

[86] PCT No.: PCT/IT92/00158

§ 371 Date: Sep. 19, 1994

§ 102(e) Date: Sep. 19, 1994

[87] PCT Pub. No.: WO93/11241

PCT Pub. Date: Jun. 10, 1993

[30] Foreign Application Priority Data

Dec. 6, 1991 [IT] Italy ................... RM91A0915

[51] Int. Cl.[6] ............... A01H 5/00; C12N 15/29; C12N 15/84; C12N 15/70; C12N 15/81

[52] U.S. Cl. ................... 800/205; 800/DIG. 25; 435/69.2; 435/172.3; 435/252.3; 435/252.33; 435/254.2; 435/320.1; 435/419; 536/23.6; 536/24.1

[58] Field of Search ............... 536/23.6, 24.1; 435/63.1, 70.1, 69.2, 172.3, 240.4, 252.3, 252.33, 254.2, 320.1, 419; 800/205, DIG. 25

[56] References Cited

U.S. PATENT DOCUMENTS 5,569,830  10/1996  Bennett et al. .................. 800/205

FOREIGN PATENT DOCUMENTS

WO 93/11241  6/1993  WIPO .

OTHER PUBLICATIONS

Abu–Goukh, A.A. and Labavitch, J.M. (1983). "The in vivo role of Bartlett pear fruit polygalacturonase inhibitors," Physiol. Plant Pathology 23:123–135.

Bock, W. et al. (1975), "Detection of the inhibition of microbial pectin and pectate lyases using inhibitors of vegetable origin," Biological Abstracts No. 60602, vol. 60(11):6494.

Brown, A.E. and Adikaram, N.K.B. (1982), "The Differential Inhibition of Pectic Enzymes from *Glomerella cingulata* and *Botrytis cinerea* by a Cell Wall Protein from *Capsicum annuum* Fruit," Phytopath. Z. 105:27–38.

Favaron, F. et al. (1994), "Purification and molecular characterization of a soybean polygalacturonase–inhibiting protein," Planta 195:80–87.

Fielding, A. (1981), "Natural Inhibitors of Fungal Polygalacturonases in Infected Fruit Tissues," J. Gen. Microbiol. 123:377–381.

Johnston, D.J. et al. (1993). "A Protein from Immature Raspberry Fruits which Inhibits Endopolygalacturonases from *Botrytis cinerea* and other Micro–organisms,"J. Exp. Bot. 44(262):971–976.

Powell, A.L.T. (1994). "Glycoprotein Inhibitors of Fungal Polygalacturonases: Expression of Pear PGIP Improves Resistance in Transgenic Tomatoes," Plant Physiol. Suppl. 105:159.

Pressey, R. (1996), "Polygalacturonase Inhibitors in Bean Pods," Phytochemistry 42(5):1267–1270.

Stotz, H.U. et al. (1993), "Molecular Characterization of a Polygalacturonase Inhibitor from *Pyrus communis* L. cv Bartlett," Plant Physiol. 102:133–138.

Stotz, H.U. et al. (1994), "Structure and expression of an inhibitor of fungal polygalacturonases from tomato," Plant Mol. Biol. 25:607–617.

Paiva et al. 1991. Plant Mol. Biol. 17(4):653–667.

Edington et al. 1991. Plant Mol. Biol. 16(1):81–94.

Broglie et al. 1991. Science 254: 1194–1197.

Lewin, R. 1987. Science 237:1570.

Reeck et al. 1987. Cell 50:667.

Desiderio et al. MPMI 10(7):852–860.

De Lorenzo et al. (1991) "Cloning of the Polygalacturonase–inhibiting Protein (PGIP) of *Phaseolus Vulgaris* L.", J. Cell Biochem. Suppl., Keystone Symposium. The Genetic Dissection of Plant Cell Processes, Jan. 10–17, 1991 vol. 15A, pp. 54, Abstract A208.

Toubart et al. "Cloning and Expression of a Polygalacturonase–inhibiting Protein PGIP of *Phaseolus Vulgaris* L.", Biological Abstracts BR43:11387 and G. Bot. Ital. 124(4):151–152 1990.

Cervone et al. (1987) "Purification and Characterization of a Polygalacturonase–inhibiting Protein from *Phaseolus Vulgaris* L.", Plant Physiol. 85:631–637.

Salvi et al. (1990) "A Polygalacturonase–inhibiting Protein in the Flowers of *Phaseolus Vulgaris* L.", J. Plant Physiol. 136:513–518.

De Lorenzo et al. (1990) "Host–pathogen Interactions. XXXVII. Abilities of the Polygalacturonase–inhibiting Proteins from Four Cultivars of *Phaseolus Vulgaris* to inhibit the Endopolygalacturonases from Three Races of *Collectotrichum lindemuthianum*", Phys. and Mol. Plant Path. 36:421–435.

(List continued on next page.)

*Primary Examiner*—David T. Fox
*Attorney, Agent, or Firm*—Greenlee, Winner & Sullivan, P.C.

[57] ABSTRACT

The gene coding for a fungal endopolygalacturonase inhibitor (PGIP) is cloned and sequenced from both *Phaseolus vulgaris* genomic and cDNA libraries. The PGIP amino acid sequence, vectors comprising the PGIP gene or parts thereof, and cells transformed by said vecors are also disclosed.

This isolated sequences are useful to transform plants, which are sensitive to fungi or microorganism pathogen activities, into plants producing the PGIP protein.

35 Claims, 5 Drawing Sheets

OTHER PUBLICATIONS

Toubart et al. (1992) "Cloning and Characterization of the Gene Encoding the Endopolygalacturonase–inhibiting Protein (PGIP) of *Phaseolus Vulgaris* L.", *The Plant Journal* 2(3):367–373.

Degrá et al. (1988) "A Polygalacturonase–inhibiting Protein in Alfalfa Callus Cultures", *J. Plant Phys.* 133:364–366.

Cervone et al. (1989) "A Plant Protein Converts a Fungal Pathogenesis Factor into an Elicitor of Plant Defense Responses", *Plant. Physiol.* 90:542–548.

Cervone et al. (1990) "Can Phaseolus PGIP Inhibit Pectic Enzymes from Microbes and Plants?", *Phytochemistry* 29:447–449 No. 2.

FIG. 7

NUCLEOTIDE SEQUENCES CODING AN ENDOPOLYGALACTURONASE INHIBITOR

BACKGROUND OF THE INVENTION

This invention relates to nucleotide sequences coding a endopolygalacturonase inhibitor.

More particularly, this invention relates to a gene coding a new protein having an inhibiting activity against the fungal endopolygalacturonase enzyme, or fractions thereof, and to the protein itself or fractions thereof. The invention relates also to recombinant vectors comprising such sequences, to cells and plants transformed by means of such recombinant vectors and to the use of such vectors and cells to produce the protein.

References are listed at the end of the specification in the order cited.

The fungal endo alpha-1,4-D-polygalactorunase enzyme (EC 3.21.15) is an important pathogenic factor for plants (1,2). The enzyme catalyzes the scission reaction of polygalacturonic acid and induces the subsequent solubilization of plant cell wall homo-alpha-1,4-D-galactorunanes, thus facilitating the penetration of fungi into plant tissues and then supplying the same fungi with nutritional substrates.

Moreover, the activity of such an enzyme could, if controlled, produce non-virulence factors, i.e. factors able to activate some plant defence mechanisms by converting plant cell wall homogalactorunanes into oligogalacturonides, which are known to stimulate phytoalexin synthesis and other defence mechanisms as well (2).

An inhibiting activity of fungal endopolygalacturonase, associated with the cell wall, named PGIP, has been detected in dicot plants.

The authors of the present invention have already detected such activity in different plant tissues of *Phaseolus vulgaris* L. (3), showing that it is specific for fungal endopolygalacturonases, with no activity against either bacterial or plant enzymes, or other pectic enzymes of microbial origin (4). Moreover, the authors found that the PGIP is able to stabilize in vitro and oligogalacturonide mixture which stimulates phytoalexins (5).

Therefore it is evident the need to purify and isolate the molecule responsible for such activity by means of cloning coding PGIP sequences. Said sequences may be inserted in suitable vectors to transform plants that are sensitive to fungi or other microorganism pathogens, into plants producing the PGIP protein on large scale. The protein could be then used with many advantages in the food industry.

SUMMARY OF THE INVENTION

Prior attempts to isolate the PGIP gene have been unsuccessful, essentially due to low levels of the protein in plant tissues.

The authors of the invention have now isolated and sequenced the PGIP protein coding DNA, both from a genomic and cDNA library, and have also identified the amino acid sequence of the PGIP protein.

An object of the present invention is a DNA fragment comprising a sequence coding a PGIP protein having an inhibiting activity of the fungal endo-alpha-1,4-D-polygalacturonase enzyme (PG), or parts thereof. Preferably said DNA fragment is of plant origin, more preferably isolated either from plants, or parts of plants, or in vitro cultured plant cells of the Phaseolus genus, most preferably of the *Phaseolus vulgaris* species.

According to a preferred embodiment said DNA fragment codes for a PGIP protein having the amino acid sequence of SEQ ID N15, or parts thereof. Alternatively said amino acid sequence SEQ ID N15 lacks or is substituted of one or more amino acids, preferably is a variant of a PGIP protein, more preferably said variant of a PGIP protein comprises the amino acid sequence SEQ ID N17, or parts thereof.

According to another embodiment said DNA fragment comprises the nucleotide sequence of SEQ ID N14, consisting of:

a coding region from nucleotide 1 to nucleotide 1026;

a 3'-end untranslated sequence from nucleotide 1027 to nucleotide 1116.

Alternatively said nucleotide sequence lacks or is substituted of one or more nucleotides, preferably comprising the nucleotide sequence of SEQ ID N16.

Another object of the invention is a DNA fragment hybridizing to at least one of DNA fragments having the sequences above described, preferably complementary to them.

Another object of the invention is a DNA fragment comprising an allele of either SEQ ID N14 or SEQ ID N16 sequences.

All of the DNA fragments according to the invention may be derived from either a genomic library, or a cDNA library or in vitro synthesis.

Another object of the invention is a substantially purified PGIP protein having an inhibiting activity for the fungine PG enzyme and being of natural or recombinant origin, or parts thereof. Preferably said substantially purified PGIP protein derives from plants, parts thereof or cultured plant cells, more preferably of the Phaseolus genus, most preferably of the *Phaseolus vulgaris* species.

According to a preferred embodiment said protein comprises the amino acid sequence of SEQ ID N15, or parts thereof, alternatively said protein lacks or is substituted of one or more amino acids, preferably said protein comprises the amino acid sequence of SEQ ID N17.

Another object of the invention is a recombinant vector comprising any one of the nucleotide sequences of the invention, preferably of plasmid or phage origin, more preferably said recombinant vector is the pAD-1 plasmid (DSM N.6821).

In a preferred embodiment said recombinant vector comprises a promoter able to express said coding PGIP nucleotide sequence, preferably said promoter is active either in bacteria, or in yeasts, or in higher plants.

Other objects of the invention are cells transformed by one of the vectors above described, preferably said cells are bacterial cells, more preferably belonging to the *Escherichia coli* species. Alternatively said cells are eukaryotic cells, preferably yeast cells, alternatively plant cells.

A further object of the invention is a process for isolating and cloning PGIP protein coding sequences, or parts thereof, comprising:

partial sequencing of the amino acid sequence of the PGIP protein;

in vitro synthesing oligonucleotides, the sequence of which is derived from said amino acid sequence;

probing a genomic or a cDNA library from plant cells with said oligonucleotides, previously labelled;

isolating positive clones, extracting the recombinant vector from a positive clone and identifying the recombinant insert from said recombinant vector;

sequencing said recombinant insert.

The invention shall be illustrated in the following examples by making references to some preferred embodiments, completed with the following figures where ;

3

BRIEF DESCRIPTION OF THE FIGURES

FIG. 7 shows a comparative analysis of PGIP coding sequences isolated from two different *cultivars* of *Phaseolus vulgaris* species.

DETAILED DESCRIPTION OF THE INVENTION

EXAMPLES

Example 1

Purification and Sequencing of PGIP Protein

Plants of *Phaseolus vulgaris L.*, Pinto *cultivar*, are grown on vermiculite under 18 hour light exposure conditions. The callus and cell suspension cultures from Pinto *cultivar* are obtained as described in (3).

The PGIP protein is purified from hypocotyls (30 µg/kg of fresh weight) by affinity chromatography on Sepharose coupled to endopolygalacturonase, as described in (6). One unit of PGIP protein is the amount able to reduce of 50% the activity of one unit of endopolygalacturonase, isolated from *Aspergillus nidulans*.

Figure 1:
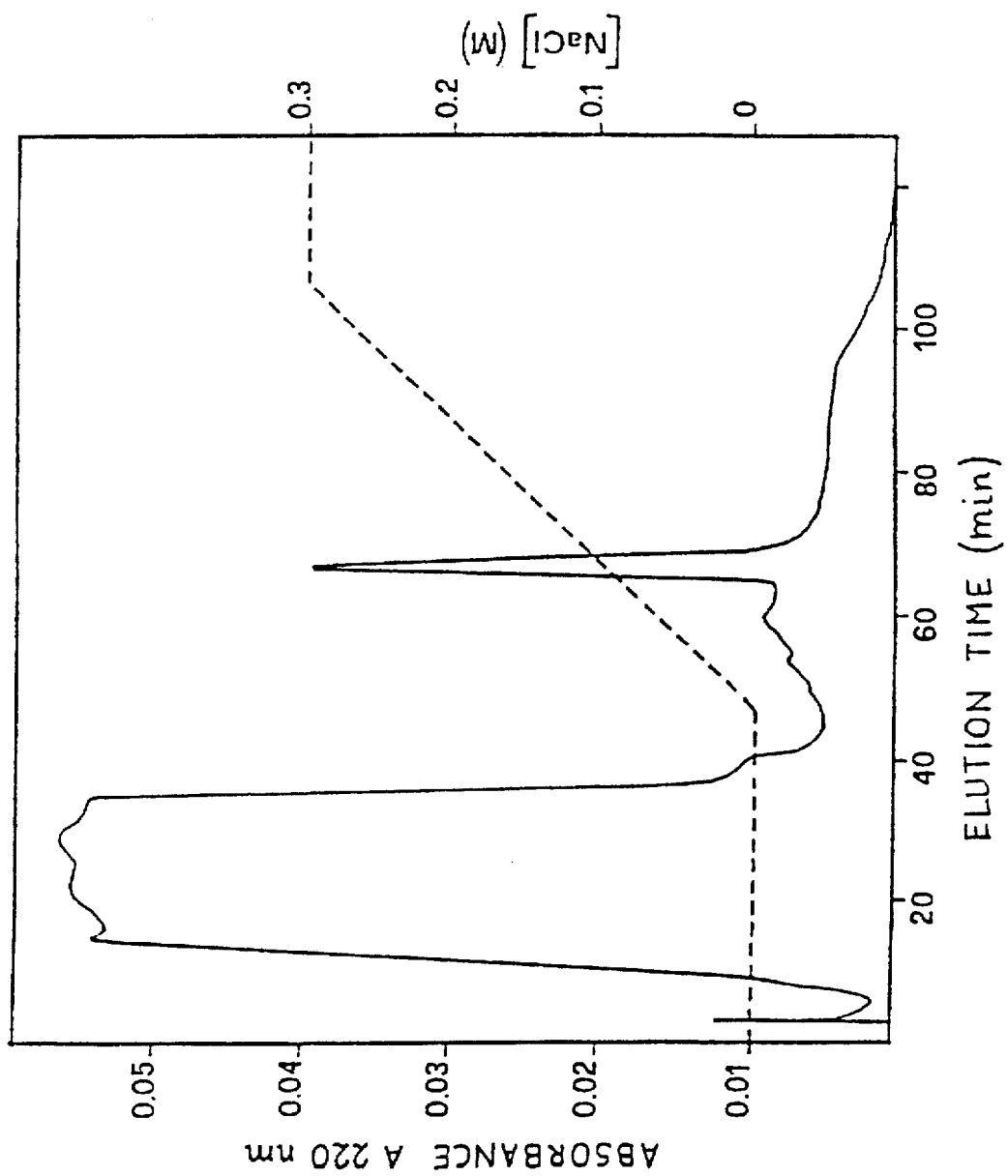
FIG. 1 shows the PGIP elution profile on Mono S column.

PGIP is then diluted at 1:4 ratio in 30 mM. Hepes pH 7.5 buffer, and loaded on Mono S column (Pharmacia), equilibrated with the same buffer. The protein is eluted with a linear gradient 0–0.3M NaCl in 20 mM Hepes pH 7.5 buffer. Approximately 90% of the loaded material having a 280 nm absorbance elutes with the excluded volume, showing no PGIP activity at all. The remaining 10% elutes with a single peak at a 0.1M NaCl and shows PGIP activity (FIG. 1). Fractions containing PGIP activity are collected and loaded again on Mono S column to concentrate the protein to 35 µg/ml.

5 µg of the protein are used to determine the N-terminal sequence, according to standard methodology. The remaining amount is digested by 1 mg/ml of TPCK (Sigma) treated trypsin in 1.0M ammonium bicarbonate pH 7.8 buffer, at 37° C. for 16 hours. The resulting peptides are separated using a binary gradient (solvent A: 0.1% TFA in water; solvent B: 0.085% TFA in 80% aqueous $CH_3CN$) at a flow rate of 0.2 ml/min. Single peaks are collected, dried, dissolved in 50 µl of solvent A and chromatographed again on the same column.

Peptides, as well as the undigested PGIP protein, are sequenced by a ABI 470A or 477A sequencer. Aminoacid sequence of the N-terminal fragment and of four tryptic fragments of the PGIP protein are shown in the Table 1 hereinbelow.

4

TABLE 1

Aminoacid sequence of the N-terminal fragment and of four tryptic peptides of PGIP protein

| Residue number | N-terminal | P-1 | P-2 | P-3 | P-4 |
|---|---|---|---|---|---|
| 1 | Glu | Ile | Leu | Ile | Ile |
| 2 | Leu | His | Phe | Tyr | Ser |
| 3 | X | Leu | Thr | X | Gly |
| 4 | Asn | Ala | Ser | Thr | Ala |
| 5 | Pro | Lys | Met | Leu | Ile |
| 6 | Glu(n) | | | Pro | Pro |
| 7 | Asp | | | Gln | Asp |
| 8 | Lys | | | Gly | Ser |
| 9 | Glu(n) | | | Leu | Tyr |
| 10 | Ala | | | Thr | Gly |
| 11 | Leu | | | Gln | Ser |
| 12 | Leu | | | Leu | Phe |
| 13 | X | | | Lys | |
| 14 | Ile | | | | |
| 15 | Lys | | | | |
| 16 | Lys | | | | |
| 17 | Asp | | | | |
| 18 | Leu | | | | |
| 19 | Gly | | | | |
| 20 | Asn | | | | |
| 21 | Pro | | | | |

X means presence of undefined residues; aa. 6 and 9 of the N-terminal sequence may be either Glu or Gln. [1]SEQ ID N1; [2]SEQ ID N2; [3]SEQ ID N3; [4]SEQ ID N4; [5]SEQ ID N5

Example 2

Nucleotide Amplification, Sequencing and Cloning

Two independent oligonucleotides are synthesized on the basis of the N-terminal sequence (N-A and N-B). A third oligonucleotide (Int) is sythesized on the basis of the peptide P-3 sequence, starting from the first nucleotide coding for aa. 6 (Pro) to the second nucleotide coding for aa. 11 (Gln). The nucleotide sequences are shown in the following Table 2.

Table 2
Primer oligonucleotides for amplification reaction and corresponding amino acid sequence
4–10 N-terminal sequence (N-A)

amino acid:
Asn—Pro—Glu—Asp—Lys—Glu—Ala  (SEQ ID N6)
        (Gln)        (Gln)

nucleotide:
5' AAT CCN GAT GAT AAA CAA CC 3'  (SEQ ID N7)
    C    C G    C    GG G 14–21 N-terminal sequence (N-B)

amino acid:
Ile—Lys—Lys—Asp—Leu—Gly—Asn—Pro  (SEQ ID N8)

nucleotide:
5' ATT AAA AAA GAT CTN GGN AAT CC 3'  (SEQ ID N9)
    C    G    G    C T        C
    A 6–11 P-3 peptide sequence (Int)

amino acid:
Pro—Gln—Gly—Leu—Thr—Gln  (SEQ ID N10)

-continued nucleotide:

3' GGN GTT CCN AAN TGN GT 5'  (SEQ ID N11)
         C                G

N means one of the four nucleotides.

N-A, N-B and Int oligonucleotides are used as primers of a polymerase chain reaction (PCR) using genomic DNA, extracted from *Phaseolus vulgaris*, Pinto *cultivar*, as template, by conventional methods (7). Polymerizing reactions are carried out on Perkin Elmer/Cetus equipment according to manufacturer's instructions. The primer hybridization is carried out at 45° C. or 50° C., depending upon using respectively degenerate or nondegenerate nucleotides. The polymerization enzyme (Amplitaq, Perkin Elmer) is used at 1 U/40 µl of reaction mix. PCR products are fractionated on a 0.8% agarose gel and dyed with ethidium bromide.

Figure 2:
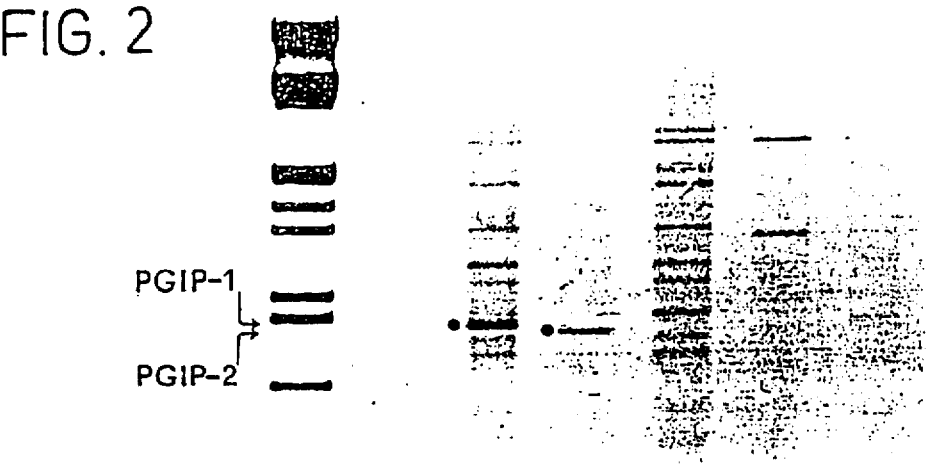
FIG. 2 shows an agarose gel electrophorosis of amplified DNA, using the following primers: A: mol weight markers; B: control; C: N-A and Int; D: N-B and Int; E: N-A; F: N-B.

A clear DNA band of appr. 0.79 kb, defined as PGIP-1, is observed (FIG. 2, line c), when using the N-A oligo. The band is missing in control reactions (FIG. 2, lines b, e, q). By using N-D and Int oligos as primers, the DNA product (PGIP-2) is of appr. 0.76 kb, i.e. 30 bp shorter than PGIP-1 (FIG. 2, line d).

Figure 3:
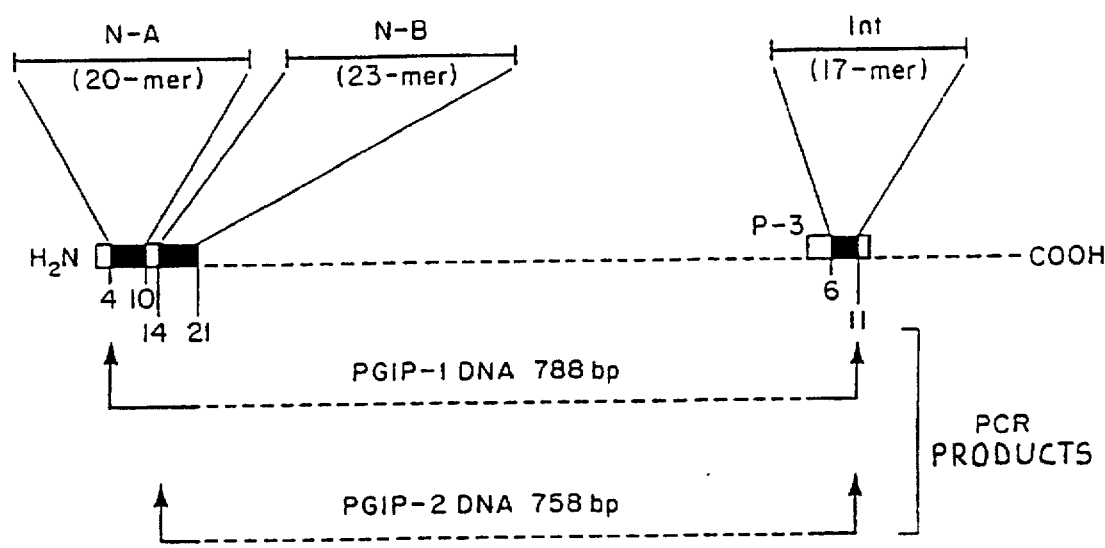
FIG. 3 shows a map of primers and of amplified DNAs.
Figure 3:
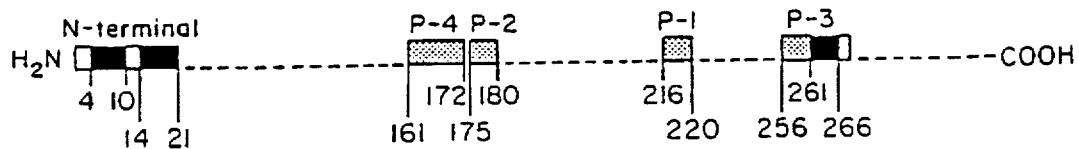

The agarose gel is transferred to nitrocellulose membrane and probed with PGIP-2, previously eluted from the agarose gel and amplified with 6 PCR cycles in presence of $P^{32}ATP$. PGIP-1 and PGIP-2 sequences hybridized with the same intensity to the radiolabelled probe. FIG. 3 shows a scheme of oligonucleotides and PCR obtained products.

The PGIP-2 fragment, eluted from the agarose gel and further amplified by PCR using N-B and Int oligonucleotides, is purified by removing the low melting point agarose and inserted into the pGEM7zf(+) vector (Promega) by conventional methods. The recombinant vector, containing the whole DNA fragment of PGIP-2, is defined as pPT-1.

The pPt-1 insert is sequenced and an open reading frame of 252 amino acids is deduced. As expected the amino acid sequence comprises sequences corresponding to the 14–21 N-terminal and to the P-3 peptide as well. Moreover it comprises sequences of the P-1, P-2 and P-4 peptides.

Example 3

Isolation of a Genomic PGIP Clone

Figure 4:
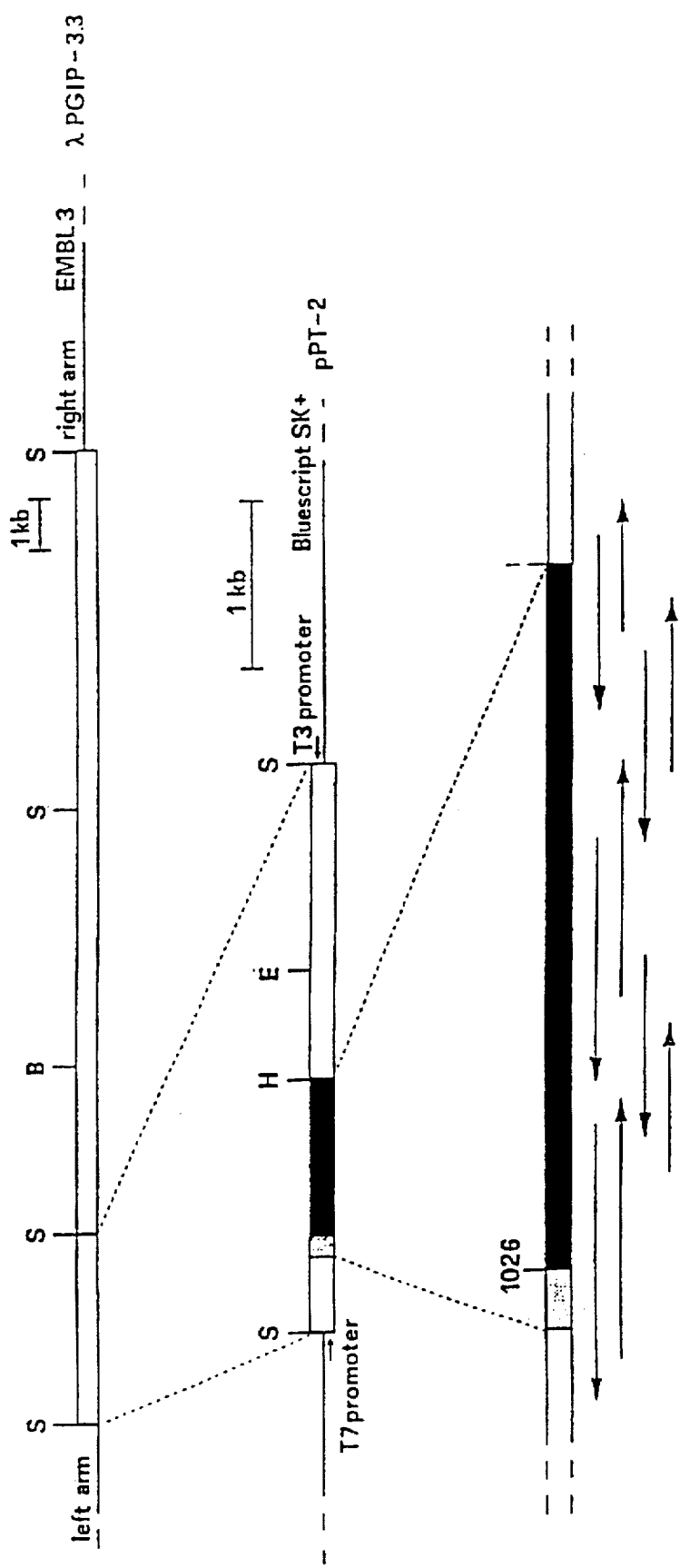
FIG. 4 shows a restriction map of lambda PGIP-3.3 and of pPT-2.

A genomic DNA library from the Saxa *cultivar* of *Phaseolus vulgaris*, obtained by partial digestion with restriction enzyme MboI, into the EMBL3 lambda vector, has been supplied by Clontech (Ca, USA). The library is probed by PCR and plaque-hybridization combination. $5 \times 10^5$ recombinant phages are probed by conventional plaque-hybridization, as described in (7), by using the radiolabelled p-PT1 insert. Positive clones are grouped in three different classes, to be further analyzed with PCR. PCR screening is performed using crude phage DNA as template and two nondegenerate primers (P21 and P22), synthesized on the basis of the p-PT1 insert sequence, whose sequences are as follows: P21: AAGGCTCTGTTCAGTTGCTT (SEQ ID N12); P22:CTATACATTGGCGGCATCAAT (SEQ ID N13). Positive clones have an expected 378 bp amplification fragment. The first class shows strong hybridization signals and is able to amplify the 378 bp fragment. The second class also shows strong hybridization signals, but amplification products from PCR are not observed. The third class shows a weaker hybridization, but gives rise to specific amplification products from PCR, other than the 378 bp fragment. Among positive clones of the first class, one clone (lambda PGIP-3.3, insert=17 kb) is selected and isolated for further analysis. A 3.3 kb SalI—SalI fragment is shown to contain the PGIP gene, as demonstrated by Southern blot analysis and PCR experiments. The fragments is subcloned in the SalI site of the Bluescript SK+ plasmid (Stratagene), resulting in a recombinant plasmid named pPt-2. The orientation and the position of the PGIP gene in the 3.3 kb cloned fragment is defined by PCR (FIG. 4), using different combination of both plasmid (T3 and T7) and PTGP specific primers (FIG. 4). It is calculated that the 3.3 kb SalI—SalI fragment comprises appr. 1860 nt upstream the first ATG, 1026 nt of coding region and 97 nt of the 3'-untranslated region, with appr. 450 nt adjacent sequences. A partial restriction map of the 17 kb genomic insert, the orientation and the PGIP position in the pPT-2 subclone are shown in FIG. 4.

Both DNA strands of the PGIP gene are sequenced; the sequence strategy is shown in FIG. 4. The whole nucleotide sequence of the PGIP coding region and of the untranslated 3' region (1116 nt) is reported in SEQ ID N14. The polyadenylation site is 97 bp downstream of the TAA stop codon. Three sequences, corresponding to putative eukaryotic polyadenylation signals, are at 42, 22 and 16 nt upstream of the polyadenylation site respectively. A comparative analysis between the genomic sequence and the relevant cDNA sequence above that no introns are present in the 345 nucleotide 3'-end gene region. Further analysis shows that no introns are present for the whole PGIP gene, as confirmed by PCR experiments. The PGIP gene DNA sequence defines a 342 amino acid PGIP protein (see SEQ ID N14 and N15). Neither the nucleotide or amino acid sequences show any significant homology with any known sequence.

Figure 5:
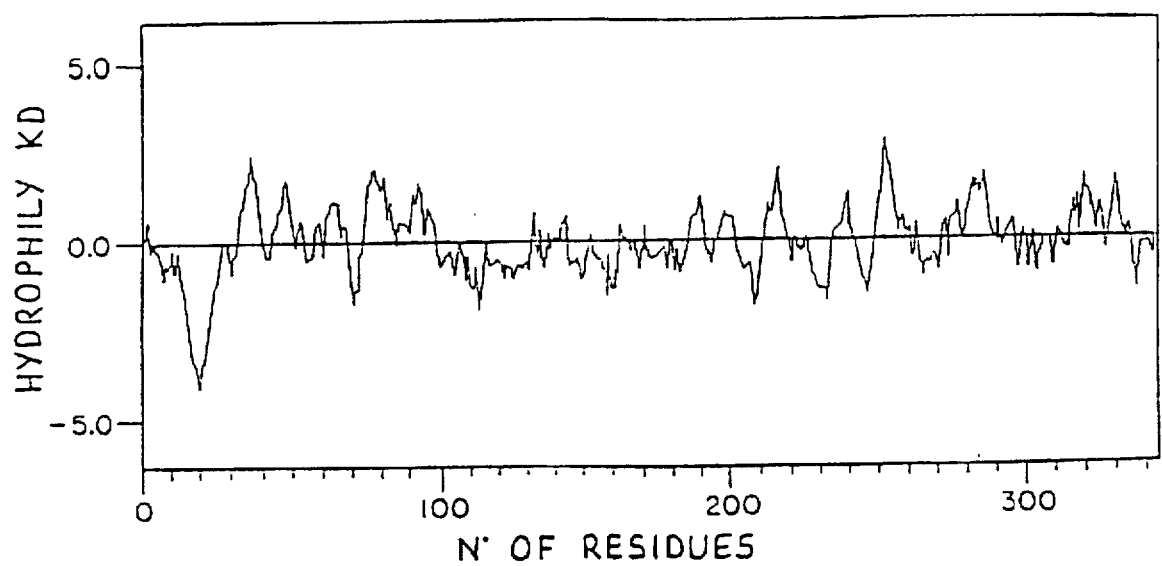
FIG. 5 shows a hydrophobicity plot of the PGIP protein.
Figure 6:
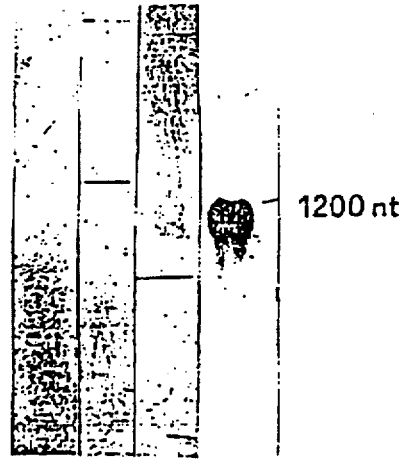
FIG. 6 shows a Northern blot by using RNAs from different plant tissues, probed with a radiolabelled pPT-1 fragment.

A hydrophobicity plot of the PGIP protein is shown in FIG. 5. The sequence includes four potential glycosylation sites.

Example 4

Northern Blot Analysis

PGIP specific mRNA levels are analysed in different plant tissues. The pPT1 purified insert is used to probe polyA+ RNA, isolated from either hypocotyls, or leaves, or flowers or suspension cultured cells of *Phaseolus vulgaris*, Pinto *cultivar*. A single 1.2 kb transcript is identified in mRNA from suspension cultured cells. The fragment is also present in other tissues, even if minor amount.

PCR experiments, using single-strand cDNA from suspension cultured cells and P-21 and P-22 as templates, shows the expected amplification of the 370 bp fragment, thus indicating that at least a fraction of the PGIP gene expression in cultured cells may be ascribed to the cloned and characterized gene.

Example 5

Analysis of PGIP Genes From Two Different *Phaseolus vulgaris cultivars*

Figure 7:
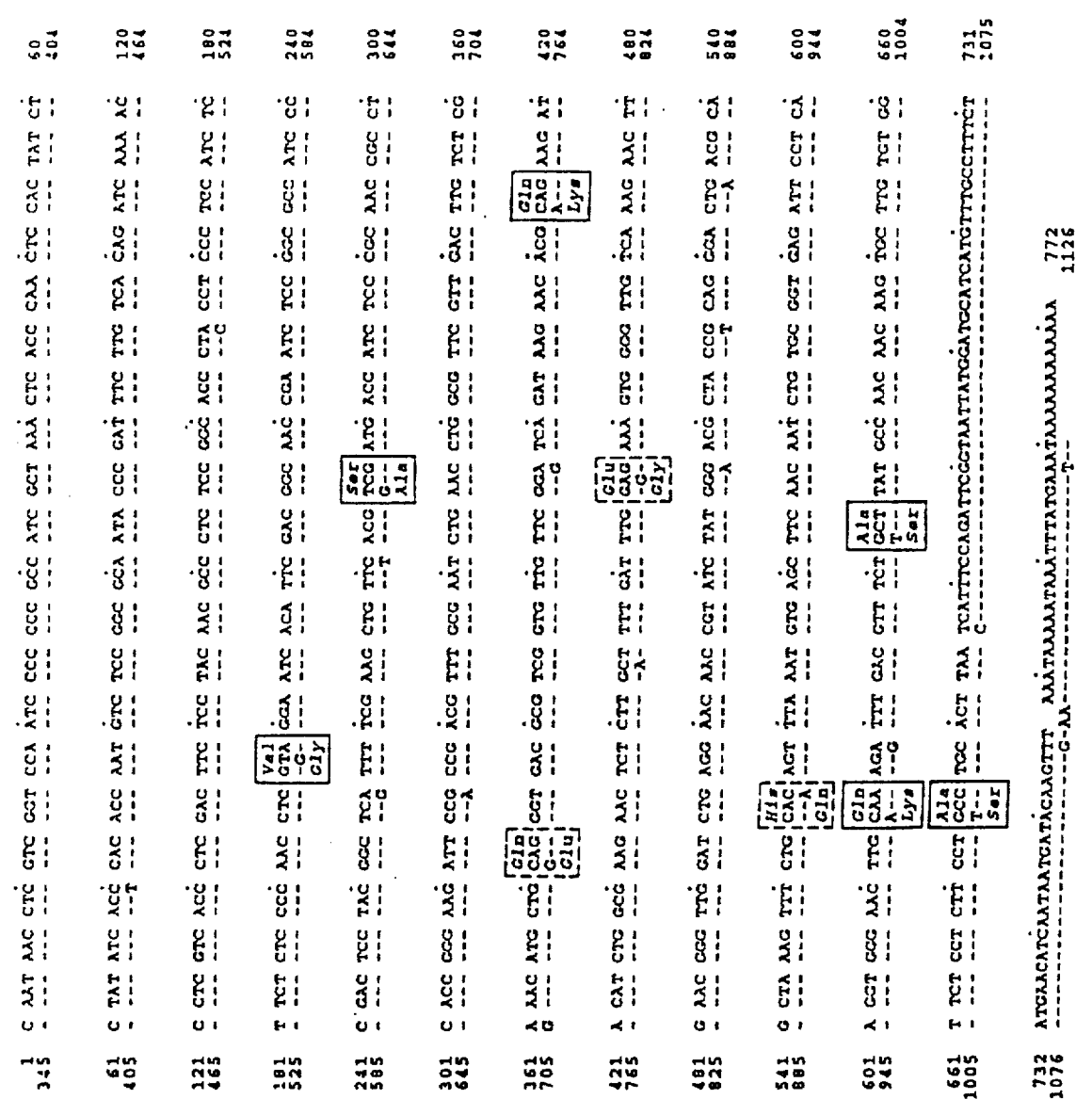

A cDNA library is made in the lambda gt11 vector from polyA$^{30}$ RNA, purified from suspension cultured cells of *Phaseolus vulgaris*, Pinto *cultivar*. By probing the cDNA library wit pPT1, a cDNA recombinant clone (lambda AD-1) containing PGIP coding sequences is isolated. The lambda AD-1 insert (842 bp) is subcloned in the Bluescript SK+ vector, named pAD-1, deposited at DSM, Germany, with the n. 6821, and sequenced. The insert represents a whole PGIP cDNA fragment and includes the polyA tail. The sequence of the pAD-1 insert is shown in SEQ ID N16. When compared to SEQ ID N14, the pAD-1 insert refers to sequence from 345 to 1116 nt of SEQ ID N14. A comparative analysis between the genomic clone from Saxa *cultivar* and the cDNA clone from Pinto *cultivar* shows a 96.4% homology of nucleotide sequence and a 97.4% homology of amino acid sequence (FIG. 7).

This invention has been described with reference to some preferred embodiments; however it is understood that any changes and/or modification could be made by anyone skilled in the art, remaining within the scope of the claims.

REFERENCES

1) Cooper, R. M. In: Plant Disease: Infection, Damage and Loss. Wood, R. K. S. & Jellis, G. J. eds. Oxford, Blackwell Scientific Publications, pp. 13–27 (1984).

2) Hahn, M. G. Bucheli, P., Cervone F., Doares, S. H., Darvill, A. G. and Albersheim, P. In: Plant-Microbe Interaction, Vol. 3, Nester, E. and Kosuge, T., eds, New York, MacMillan Press, pp. 131–181 (1989).

3) Salvi, G., Giarizzo, F., De Lorenzo, G. and Cervone, F. J. Plant Physiol, 136, 513–518 (1990).

4) Cervone, F., De Lorenzo, G. Pressey, R., Darvill, A., and Albersheim, P. Phytochemistry 29, 447–449 (1990).

5) Cervone F., Hahn, N. G., De Lorenzo, G., Darvill, A. and Albersheim, P. Plant Physiology, 90, 542–548 (1989).

6) Degra, L. Salvi, G., Mariotti, D., De Lorenzo, G. and Cervone, F. J. Plant Physiol., 133, 364–366 (1988).

7) Sambrook, D., Fritsch, E. F., Naniatis, T. In: Molecular Cloning: A Laboratory Manual, 2nd ed., vols.1, 2, 3, CSH Lab Press (1989).

---

We claim:

1. An isolated DNA fragment, or the complement thereof, encoding a protein having an inhibiting activity for a fungal polygalacturonase enzyme derived from Phaseolus plants, parts thereof or cultured plant cells of a plant of the genus Phaseolus.

2. An isolated DNA fragment according to claim 1 wherein said Phaseolus plant is of the species *Phaseolus vulgaris*.

3. An isolated DNA fragment according to claim 1 which encodes a protein comprising the amino acid sequence of SEQ ID No. 15 or SEQ ID No. 17.

4. An isolated DNA according to claim 3 which encodes a protein comprising the amino acid sequence of SEQ ID N15 extending from amino acid 1 to amino acid 342.

5. An isolated DNA according to claim 4 which encodes a protein having the amino acid sequence of SEQ ID N15.

6. An isolated DNA according to claim 3 which encodes a protein having the amino acid sequence of SEQ ID N15 extending from amino acid 1 to amino acid 342.

7. An isolated DNA fragment, or complement thereof, which encodes a protein derived from plants, parts thereof or cultured plant cells, said protein having an inhibitory activity for a fungal polygalacturonase enzyme and comprising a substituted SEQ ID No. 15 in which up to nine amino acids are substituted.

8. An isolated DNA fragment according to claim 7 which encodes a protein comprising the amino acid sequence of SEQ ID N17.

9. An isolated DNA fragment according to claim 1 comprising the coding region from nucleotide 1 to nucleotide 1026 of SEQ ID No. 14 or the coding region from nucleotide 2 to 685 of SEQ ID No. 16.

10. An isolated DNA fragment according to claim 9 further comprising a 3'-untranslated sequence from nucleotide 1027 to nucleotide 1116 of SEQ ID N14.

11. An isolated DNA fragment according to claim 1 comprising an allele of either SEQ ID N14 or SEQ ID N16 sequences.

12. A plant transformed with a DNA fragment according to claim 1 to thereby produce a PGIP protein having an inhibiting activity for a fungal PG enzyme.

13. A plant according to claim 12 which prior to transformation does not produce said PGIP protein.

14. The plant of claim 12 that is a dicot.

15. A recombinant vector comprising a DNA fragment according to claim 1.

16. A recombinant vector according to claim 15 wherein the vector is of plasmid or phage origin.

17. A recombinant vector comprising a DNA fragment according to claim 3.

18. A recombinant vector according to claim 17 wherein said vector is the pAD-1 plasmid.

19. A recombinant vector according to claim 15 wherein said vector comprises a promoter capable of expressing said coding PGIP nucleotide sequence.

20. A recombinant vector according to claim 19 wherein said promoter is active in bacteria, in yeasts or in higher plants.

21. Cells transformed by a vector according to claim 15.

22. Cells according to claim 21 which are bacterial cells.

23. Cells according to claim 22 which are of the species *Escherichia coli*.

24. Cells according to claim 21 which are higher plant cells.

25. Cells according to claim 21 which are yeast cells.

26. An isolated DNA fragment according to claim 7 wherein said plant is a plant of the genus Phaseolus.

27. An isolated DNA fragment according to claim 26 wherein said plant is of the species *Phaseolus vulgaris*.

28. A plant transformed with a DNA fragment according to claim 3 to thereby produce a PGIP protein having an inhibiting activity for a fungal PG system.

29. A plant transformed with a DNA fragment according to claim 7 to thereby produce a PGIP protein having an inhibiting activity for a fungal PG enzyme.

30. A process for making a plant which produces an increased level of PGIP which comprises transforming said plant with a DNA fragment according to claim 1 such that PGIP is thereby produced.

31. A process for making a plant which produces an increased level of PGIP which comprises transforming said plant with a DNA fragment according to claim 3 such that PGIP is thereby produced.

32. A process for making a plant which produces an increased level of PGIP which comprises transforming said plant with a DNA fragment according to claim 7 such that PGIP is thereby produced.

33. A recombinant vector comprising a DNA fragment according to claim 7.

34. Cells transformed by a vector according to claim 17.

35. Cells transformed by a vector according to claim 33.

* * * * *

UNITED STATES PATENT AND TRADEMARK OFFICE
CERTIFICATE OF CORRECTION

PATENT NO.   : 5,744,692
DATED        : Apr. 28, 1998
INVENTOR(S)  : Cervone et al.

It is certified that error appears in the above-identified patent and that said Letters Patent is hereby corrected as shown below:

Col. 1, line 3, please insert the following directly before the

"BACKGROUND OF THE INVENTION"

--STATEMENT REGARDING FEDERALLY SPONSORED RESEARCH OR DEVELOPMENT

This invention was made with Government support under Contract No. DE-FG02-96ER20221 awarded by the Department of Energy.
The Government has certain rights in this invention.--

Signed and Sealed this

First Day of August, 2000

Q. TODD DICKINSON

*Attest:*

*Attesting Officer*   *Director of Patents and Trademarks*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Phaseolus vulgaris
        ( B ) STRAIN: Pinto ( x i ) SEQUENCE DESCRIPTION: SEQ ID NO:1:

```
Glu  Leu  Xaa  Asn  Pro  Glx  Asp  Lys  Glx  Ala  Leu  Leu  Xaa  Ile  Lys  Lys
 1                  5                        10                       15

Asp  Leu  Gly  Asn  Pro
                 20
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Phaseolus vulgaris
        ( B ) STRAIN: Pinto ( x i ) SEQUENCE DESCRIPTION: SEQ ID NO:2:

```
Ile  His  Leu  Ala  Lys
```

1          5

( 2 ) INFORMATION FOR SEQ ID NO:3:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
    ( A ) ORGANISM: Phaseolus vulgaris
    ( B ) STRAIN: Pinto ( x i ) SEQUENCE DESCRIPTION: SEQ ID NO:3:

Leu  Phe  Thr  Ser  Met
1              5

( 2 ) INFORMATION FOR SEQ ID NO:4:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
    ( A ) ORGANISM: Phaseolus vulgaris
    ( B ) STRAIN: Pinto ( x i ) SEQUENCE DESCRIPTION: SEQ ID NO:4:

Ile  Trp  Xaa  Thr  Leu  Pro  Gln  Gly  Leu  Thr  Gln  Leu  Lys
1              5                              10

( 2 ) INFORMATION FOR SEQ ID NO:5:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
    ( A ) ORGANISM: Phaseolus vulgaris
    ( B ) STRAIN: Pinto ( x i ) SEQUENCE DESCRIPTION: SEQ ID NO:5:

Ile  Ser  Gly  Ala  Ile  Pro  Asp  Ser  Tyr  Gly  Ser  Phe
1              5                              10

( 2 ) INFORMATION FOR SEQ ID NO:6:

( i ) SEQUENCE CHARACTERISTICS:
    ( A ) LENGTH: 7 amino acids
    ( B ) TYPE: amino acid

```
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
            ( A ) ORGANISM: Phaseolus vulgaris
            ( B ) STRAIN: Pinto ( x i ) SEQUENCE DESCRIPTION: SEQ ID NO:6:

Asn  Pro  Glx  Asp  Lys  Glx  Ala
    1                   5
```

( 2 ) INFORMATION FOR SEQ ID NO:7:

```
    ( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: synthetic primer/probe ( i i i ) HYPOTHETICAL: YES ( i v ) ANTI-SENSE: NO ( x i ) SEQUENCE DESCRIPTION: SEQ ID NO:7:
```

AAYCCNSARG AYAARSARCC                       20

( 2 ) INFORMATION FOR SEQ ID NO:8:

```
    ( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
            ( A ) ORGANISM: Phaseolus vulgaris
            ( B ) STRAIN: Pinto ( x i ) SEQUENCE DESCRIPTION: SEQ ID NO:8:

Ile  Lys  Lys  Asp  Leu  Gly  Asn  Pro
    1                   5
```

( 2 ) INFORMATION FOR SEQ ID NO:9:

```
    ( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: synthetic primer/probe ( i i i ) HYPOTHETICAL: YES ( i v ) ANTI-SENSE: NO ( x i ) SEQUENCE DESCRIPTION: SEQ ID NO:9:
```

ATHAARAARG AYYTNGGNAA YCC                   23

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Phaseolus vulgaris
        ( B ) STRAIN: Pinto ( x i ) SEQUENCE DESCRIPTION: SEQ ID NO:10:

Pro  Gln  Gly  Leu  Thr  Gln
    1                        5

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: synthetic primer/probe ( i i i ) HYPOTHETICAL: YES ( i v ) ANTI-SENSE: NO ( x i ) SEQUENCE DESCRIPTION: SEQ ID NO:11:

GGNGTYCCNR ANTGNGT                                                          17

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: synthetic primer/probe ( i i i ) HYPOTHETICAL: NO ( i v ) ANTI-SENSE: NO ( v i ) ORIGINAL SOURCE:
        ( A ) ORGANISM: Phaseolus vulgaris
        ( B ) STRAIN: Pinto ( v i i ) IMMEDIATE SOURCE:
        ( B ) CLONE: P21

( x i ) SEQUENCE DESCRIPTION: SEQ ID NO:12:

AAGGCTCTGT TCAGTTGCTT                                                   20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic primer/probe ( i i i ) HYPOTHETICAL: NO ( i v ) ANTI-SENSE: NO ( v i ) ORIGINAL SOURCE:
  ( A ) ORGANISM: Phaseolus vulgaris
  ( B ) STRAIN: Pinto ( v i i ) IMMEDIATE SOURCE:
  ( B ) CLONE: P22

( x i ) SEQUENCE DESCRIPTION: SEQ ID NO:13:

CTATACATTG GCGGCATCAA T    21

( 2 ) INFORMATION FOR SEQ ID NO:14:

( i ) SEQUENCE CHARACTERISTICS:
    ( A ) LENGTH: 1116 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Phaseolus vulgaris
    ( B ) STRAIN: Saxa ( v i i ) IMMEDIATE SOURCE:
    ( B ) CLONE: lambda PGIP-3.3

( i x ) FEATURE:
    ( A ) NAME/KEY: CDS
    ( B ) LOCATION: 1..1026

( i x ) FEATURE:
    ( A ) NAME/KEY: 3'UTR
    ( B ) LOCATION: 1027..1116

( x i ) SEQUENCE DESCRIPTION: SEQ ID NO:14:

| ATG | ACT | CAA | TTC | AAT | ATC | CCA | GTA | ACC | ATG | TCT | TCA | AGC | TTA | AGC | ATA | 48 |
| Met | Thr | Gln | Phe | Asn | Ile | Pro | Val | Thr | Met | Ser | Ser | Ser | Leu | Ser | Ile | |
| 1 | | | | 5 | | | | | 10 | | | | | 15 | | |

| ATT | TTG | GTC | ATT | CTT | GTA | TCT | TTG | AGA | ACT | GCA | CTC | TCA | GAG | CTA | TGC | 96 |
| Ile | Leu | Val | Ile | Leu | Val | Ser | Leu | Arg | Thr | Ala | Leu | Ser | Glu | Leu | Cys | |
| | | | 20 | | | | | 25 | | | | | 30 | | | |

| AAC | CCA | CAA | GAT | AAG | CAA | GCC | CTT | CTC | CAA | ATC | AAG | AAA | GAC | CTT | GGC | 144 |
| Asn | Pro | Gln | Asp | Lys | Gln | Ala | Leu | Leu | Gln | Ile | Lys | Lys | Asp | Leu | Gly | |
| | | 35 | | | | | 40 | | | | | 45 | | | | |

| AAC | CCA | ACC | ACT | CTC | TCT | TCA | TGG | CTT | CCA | ACC | ACC | GAC | TGT | TGT | AAC | 192 |
| Asn | Pro | Thr | Thr | Leu | Ser | Ser | Trp | Leu | Pro | Thr | Thr | Asp | Cys | Cys | Asn | |
| | 50 | | | | | 55 | | | | | 60 | | | | | |

| AGA | ACC | TGG | CTA | GGT | GTT | TTA | TGC | GAC | ACC | GAC | ACC | CAA | ACA | TAT | CGC | 240 |
| Arg | Thr | Trp | Leu | Gly | Val | Leu | Cys | Asp | Thr | Asp | Thr | Gln | Thr | Tyr | Arg | |
| 65 | | | | | 70 | | | | | 75 | | | | | 80 | |

| GTC | AAC | AAC | CTC | GAC | CTC | TCC | GGC | CAT | AAC | CTC | CCA | AAA | CCC | TAC | CCT | 288 |
| Val | Asn | Asn | Leu | Asp | Leu | Ser | Gly | His | Asn | Leu | Pro | Lys | Pro | Tyr | Pro | |
| | | | | 85 | | | | | 90 | | | | | 95 | | |

| ATC | CCT | TCC | TCC | CTC | GCC | AAC | CTC | CCC | TAC | CTC | AAT | TTT | CTA | TAC | ATT | 336 |
| Ile | Pro | Ser | Ser | Leu | Ala | Asn | Leu | Pro | Tyr | Leu | Asn | Phe | Leu | Tyr | Ile | |
| | | | | 100 | | | | | 105 | | | | | 110 | | |

| GGC | GGC | ATC | AAT | AAC | CTC | GTC | GGT | CCA | ATC | CCC | CCC | GCC | ATC | GCT | AAA | 384 |
| Gly | Gly | Ile | Asn | Asn | Leu | Val | Gly | Pro | Ile | Pro | Pro | Ala | Ile | Ala | Lys | |
| | | | 115 | | | | | 120 | | | | | 125 | | | |

| CTC | ACC | CAA | CTC | CAC | TAT | CTC | TAT | ATC | ACT | CAC | ACC | AAT | GTC | TCC | GGC | 432 |

|   |   |   |   |   |   |   |   |   |   |   |   |   |   |   |   |
|---|---|---|---|---|---|---|---|---|---|---|---|---|---|---|---|
| Leu | Thr | Gln | Leu | His | Tyr | Leu | Tyr | Ile | Thr | His | Thr | Asn | Val | Ser | Gly |
|  | 130 |  |  |  | 135 |  |  |  |  | 140 |  |  |  |  |  |

```
GCA  ATA  CCC  GAT  TTC  TTG  TCA  CAG  ATC  AAA  ACC  CTC  GTC  ACC  CTC  GAC        480
Ala  Ile  Pro  Asp  Phe  Leu  Ser  Gln  Ile  Lys  Thr  Leu  Val  Thr  Leu  Asp
145                      150                      155                      160

TTC  TCC  TAC  AAC  GCC  CTC  TCC  GGC  ACC  CTC  CCT  CCC  TCC  ATC  TCT  TCT        528
Phe  Ser  Tyr  Asn  Ala  Leu  Ser  Gly  Thr  Leu  Pro  Pro  Ser  Ile  Ser  Ser
                         165                      170                      175

CTC  CCC  AAC  CTC  GGA  GGA  ATC  ACA  TTC  GAC  GGC  AAC  CGA  ATC  TCC  GGC        576
Leu  Pro  Asn  Leu  Gly  Gly  Ile  Thr  Phe  Asp  Gly  Asn  Arg  Ile  Ser  Gly
               180                      185                      190

GCC  ATC  CCC  GAC  TCC  TAC  GGC  TCG  TTT  TCG  AAG  CTG  TTT  ACG  GCG  ATG        624
Ala  Ile  Pro  Asp  Ser  Tyr  Gly  Ser  Phe  Ser  Lys  Leu  Phe  Thr  Ala  Met
          195                      200                      205

ACC  ATC  TCC  CGC  AAC  CGC  CTC  ACC  GGG  AAG  ATT  CCA  CCG  ACG  TTT  GCG        672
Thr  Ile  Ser  Arg  Asn  Arg  Leu  Thr  Gly  Lys  Ile  Pro  Pro  Thr  Phe  Ala
     210                      215                      220

AAT  CTG  AAC  CTG  GCG  TTC  GTT  GAC  TTG  TCT  CGG  AAC  ATG  CTG  GAG  GGT        720
Asn  Leu  Asn  Leu  Ala  Phe  Val  Asp  Leu  Ser  Arg  Asn  Met  Leu  Glu  Gly
225                      230                      235                      240

GAC  GCG  TCG  GTG  TTG  TTC  GGG  TCA  GAT  AAG  AAC  ACG  AAG  AAG  ATA  CAT        768
Asp  Ala  Ser  Val  Leu  Phe  Gly  Ser  Asp  Lys  Asn  Thr  Lys  Lys  Ile  His
                         245                      250                      255

CTG  GCG  AAG  AAC  TCT  CTT  GCT  TTT  GAT  TTG  GGG  AAA  GTG  GGG  TTG  TCA        816
Leu  Ala  Lys  Asn  Ser  Leu  Ala  Phe  Asp  Leu  Gly  Lys  Val  Gly  Leu  Ser
               260                      265                      270

AAG  AAC  TTG  AAC  GGG  TTG  GAT  CTG  AGG  AAC  AAC  CGT  ATC  TAT  GGA  ACG        864
Lys  Asn  Leu  Asn  Gly  Leu  Asp  Leu  Arg  Asn  Asn  Arg  Ile  Tyr  Gly  Thr
          275                      280                      285

CTA  CCT  CAG  GGA  CTA  ACG  CAG  CTA  AAG  TTT  CTG  CAA  AGT  TTA  AAT  GTG        912
Leu  Pro  Gln  Gly  Leu  Thr  Gln  Leu  Lys  Phe  Leu  Gln  Ser  Leu  Asn  Val
     290                      295                      300

AGC  TTC  AAC  AAT  CTG  TGC  GGT  GAG  ATT  CCT  CAA  GGT  GGG  AAC  TTG  AAA        960
Ser  Phe  Asn  Asn  Leu  Cys  Gly  Glu  Ile  Pro  Gln  Gly  Gly  Asn  Leu  Lys
305                      310                      315                      320

AGG  TTT  GAC  GTT  TCT  TCT  TAT  GCC  AAC  AAC  AAG  TGC  TTG  TGT  GGT  TCT       1008
Arg  Phe  Asp  Val  Ser  Ser  Tyr  Ala  Asn  Asn  Lys  Cys  Leu  Cys  Gly  Ser
                         325                      330                      335

CCT  CTT  CCT  TCC  TGC  ACT  TAACCATTTC  CAGATTCGGT  AATTATGGAT                      1056
Pro  Leu  Pro  Ser  Cys  Thr
                    340

GCATCATGTT TGCCTTTCTA TGAACATCAA TAATGATACA AGTGTAAAAA TAAAAAATTA                     1116
```

( 2 ) INFORMATION FOR SEQ ID NO:15:

( i ) SEQUENCE CHARACTERISTICS:
        ( A ) LENGTH: 342 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Thr  Gln  Phe  Asn  Ile  Pro  Val  Thr  Met  Ser  Ser  Ser  Leu  Ser  Ile
 1                    5                     10                        15

Ile  Leu  Val  Ile  Leu  Val  Ser  Leu  Arg  Thr  Ala  Leu  Ser  Glu  Leu  Cys
               20                       25                     30

Asn  Pro  Gln  Asp  Lys  Gln  Ala  Leu  Leu  Gln  Ile  Lys  Lys  Asp  Leu  Gly
          35                        40                       45

Asn  Pro  Thr  Thr  Leu  Ser  Ser  Trp  Leu  Pro  Thr  Thr  Asp  Cys  Cys  Asn
     50                        55                        60
```

| Arg<br>65 | Thr | Trp | Leu | Gly | Val<br>70 | Leu | Cys | Asp | Thr | Asp<br>75 | Thr | Gln | Thr | Tyr | Arg<br>80 |

Val Asn Asn Leu Asp Leu Ser Gly His Asn Leu Pro Lys Pro Tyr Pro
           85                  90              95

Ile Pro Ser Ser Leu Ala Asn Leu Pro Tyr Leu Asn Phe Leu Tyr Ile
           100                 105             110

Gly Gly Ile Asn Asn Leu Val Gly Pro Ile Pro Pro Ala Ile Ala Lys
           115             120             125

Leu Thr Gln Leu His Tyr Leu Tyr Ile Thr His Thr Asn Val Ser Gly
    130                  135             140

Ala Ile Pro Asp Phe Leu Ser Gln Ile Lys Thr Leu Val Thr Leu Asp
145             150                 155                         160

Phe Ser Tyr Asn Ala Leu Ser Gly Thr Leu Pro Pro Ser Ile Ser Ser
             165                 170                 175

Leu Pro Asn Leu Gly Gly Ile Thr Phe Asp Gly Asn Arg Ile Ser Gly
         180                 185                 190

Ala Ile Pro Asp Ser Tyr Gly Ser Phe Ser Lys Leu Phe Thr Ala Met
         195                 200                 205

Thr Ile Ser Arg Asn Arg Leu Thr Gly Lys Ile Pro Pro Thr Phe Ala
    210                 215                 220

Asn Leu Asn Leu Ala Phe Val Asp Leu Ser Arg Asn Met Leu Glu Gly
225             230                 235                         240

Asp Ala Ser Val Leu Phe Gly Ser Asp Lys Asn Thr Lys Lys Ile His
             245                 250                 255

Leu Ala Lys Asn Ser Leu Ala Phe Asp Leu Gly Lys Val Gly Leu Ser
         260                 265                 270

Lys Asn Leu Asn Gly Leu Asp Leu Arg Asn Asn Arg Ile Tyr Gly Thr
         275                 280                 285

Leu Pro Gln Gly Leu Thr Gln Leu Lys Phe Leu Gln Ser Leu Asn Val
    290                 295                 300

Ser Phe Asn Asn Leu Cys Gly Glu Ile Pro Gln Gly Gly Asn Leu Lys
305             310                 315                         320

Arg Phe Asp Val Ser Ser Tyr Ala Asn Asn Lys Cys Leu Cys Gly Ser
             325                 330                 335

Pro Leu Pro Ser Cys Thr
             340

( 2 ) INFORMATION FOR SEQ ID NO:16:

( i ) SEQUENCE CHARACTERISTICS:
        ( A ) LENGTH: 792 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Phaseolus vulgaris
        ( B ) STRAIN: Pinto ( v i i ) IMMEDIATE SOURCE:
        ( B ) CLONE: pAD-1 (DSM No.6821)

( i x ) FEATURE:
        ( A ) NAME/KEY: CDS
        ( B ) LOCATION: 2..685

( i x ) FEATURE:
    ( A ) NAME/KEY: 3'UTR
    ( B ) LOCATION: 686..792

( x i ) SEQUENCE DESCRIPTION: SEQ ID NO:16:

```
C  AAT  AAC  CTC  GTC  GGT  CCA  ATC  CCC  CCC  GCC  ATC  GCT  AAA  CTC  ACC      46
   Asn  Asn  Leu  Val  Gly  Pro  Ile  Pro  Pro  Ala  Ile  Ala  Lys  Leu  Thr
   1                 5                        10                       15

CAA  CTC  CAC  TAT  CTC  TAT  ATC  ACC  CAC  ACC  AAT  GTC  TCC  GGC  GCA  ATA    94
Gln  Leu  His  Tyr  Leu  Tyr  Ile  Thr  His  Thr  Asn  Val  Ser  Gly  Ala  Ile
                    20                       25                       30

CCC  GAT  TTC  TTG  TCA  CAG  ATC  AAA  ACC  CTC  GTC  ACC  CTC  GAC  TTC  TCC   142
Pro  Asp  Phe  Leu  Ser  Gln  Ile  Lys  Thr  Leu  Val  Thr  Leu  Asp  Phe  Ser
                    35                       40                       45

TAC  AAC  GCC  CTC  TCC  GGC  ACC  CTA  CCT  CCC  TCC  ATC  TCT  TCT  CTC  CCC   190
Tyr  Asn  Ala  Leu  Ser  Gly  Thr  Leu  Pro  Pro  Ser  Ile  Ser  Ser  Leu  Pro
          50                       55                       60

AAC  CTC  GTA  GGA  ATC  ACA  TTC  GAC  GGC  AAC  CGA  ATC  TCC  GGC  GCC  ATC   238
Asn  Leu  Val  Gly  Ile  Thr  Phe  Asp  Gly  Asn  Arg  Ile  Ser  Gly  Ala  Ile
          65                       70                       75

CCC  GAC  TCC  TAC  GGC  TCA  TTT  TCG  AAG  CTG  TTC  ACG  TCG  ATG  ACC  ATC   286
Pro  Asp  Ser  Tyr  Gly  Ser  Phe  Ser  Lys  Leu  Phe  Thr  Ser  Met  Thr  Ile
80                       85                       90                       95

TCC  CGC  AAC  CGC  CTC  ACC  GGG  AAG  ATT  CCG  CCG  ACG  TTT  GCG  AAT  CTG   334
Ser  Arg  Asn  Arg  Leu  Thr  Gly  Lys  Ile  Pro  Pro  Thr  Phe  Ala  Asn  Leu
               100                      105                      110

AAC  CTG  GCG  TTC  GTT  GAC  TTG  TCT  CGA  AAC  ATG  CTG  CAG  GGT  GAC  GCG   382
Asn  Leu  Ala  Phe  Val  Asp  Leu  Ser  Arg  Asn  Met  Leu  Gln  Gly  Asp  Ala
               115                      120                      125

TCG  GTG  TTG  TTC  GGA  TCA  GAT  AAG  AAC  ACG  CAG  AAG  ATA  CAT  CTG  GCG   430
Ser  Val  Leu  Phe  Gly  Ser  Asp  Lys  Asn  Thr  Gln  Lys  Ile  His  Leu  Ala
               130                      135                      140

AAG  AAC  TCT  CTT  GCT  TTT  GAT  TTG  GAG  AAA  GTG  GGG  TTG  TCA  AAG  AAC   478
Lys  Asn  Ser  Leu  Ala  Phe  Asp  Leu  Glu  Lys  Val  Gly  Leu  Ser  Lys  Asn
     145                      150                      155

TTG  AAC  GGG  TTG  GAT  CTG  AGG  AAC  AAC  CGT  ATC  TAT  GGG  ACG  CTA  CCG   526
Leu  Asn  Gly  Leu  Asp  Leu  Arg  Asn  Asn  Arg  Ile  Tyr  Gly  Thr  Leu  Pro
160                      165                      170                      175

CAG  GGA  CTG  ACG  CAG  CTA  AAG  TTT  CTG  CAC  AGT  TTA  AAT  GTG  AGC  TTC   574
Gln  Gly  Leu  Thr  Gln  Leu  Lys  Phe  Leu  His  Ser  Leu  Asn  Val  Ser  Phe
                    180                      185                      190

AAC  AAT  CTG  TGC  GGT  GAG  ATT  CCT  CAA  GGT  GGG  AAC  TTG  CAA  ACA  TTT   622
Asn  Asn  Leu  Cys  Gly  Glu  Ile  Pro  Gln  Gly  Gly  Asn  Leu  Gln  Thr  Phe
               195                      200                      205

CAC  GTT  TCT  GCT  TAT  GCC  AAC  AAC  AAG  TGC  TTG  TGT  GGT  TCT  CCT  CTT   670
His  Val  Ser  Ala  Tyr  Ala  Asn  Asn  Lys  Cys  Leu  Cys  Gly  Ser  Pro  Leu
          210                      215                      220

CCT  GCC  TGC  ACT  TAATCATTTC  CAGATTCGGT  AATTATGGAT  GCATCATGTT             722
Pro  Ala  Cys  Thr
          225

TGCCTTTCTA TGAACATCAA TAATGATACA AGTTTAAATA AAAATAAATT TATGAAATAA              782

AAAAAAAAAA                                                                     792
```

( 2 ) INFORMATION FOR SEQ ID NO:17:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Asn Asn Leu Val Gly Pro Ile Pro Pro Ala Ile Ala Lys Leu Thr Gln
 1            5                   10                  15
Leu His Tyr Leu Tyr Ile Thr His Thr Asn Val Ser Gly Ala Ile Pro
            20              25                  30
Asp Phe Leu Ser Gln Ile Lys Thr Leu Val Thr Leu Asp Phe Ser Tyr
        35              40                  45
Asn Ala Leu Ser Gly Thr Leu Pro Pro Ser Ile Ser Ser Leu Pro Asn
    50              55                  60
Leu Val Gly Ile Thr Phe Asp Gly Asn Arg Ile Ser Gly Ala Ile Pro
65              70                  75                      80
Asp Ser Tyr Gly Ser Phe Ser Lys Leu Phe Thr Ser Met Thr Ile Ser
                85                  90                  95
Arg Asn Arg Leu Thr Gly Lys Ile Pro Pro Thr Phe Ala Asn Leu Asn
            100             105                     110
Leu Ala Phe Val Asp Leu Ser Arg Asn Met Leu Gln Gly Asp Ala Ser
        115             120                 125
Val Leu Phe Gly Ser Asp Lys Asn Thr Gln Lys Ile His Leu Ala Lys
    130             135                     140
Asn Ser Leu Ala Phe Asp Leu Glu Lys Val Gly Leu Ser Lys Asn Leu
145             150                 155                     160
Asn Gly Leu Asp Leu Arg Asn Asn Arg Ile Tyr Gly Thr Leu Pro Gln
            165                     170                 175
Gly Leu Thr Gln Leu Lys Phe Leu His Ser Leu Asn Val Ser Phe Asn
            180                 185                 190
Asn Leu Cys Gly Glu Ile Pro Gln Gly Gly Asn Leu Gln Thr Phe His
        195                 200                 205
Val Ser Ala Tyr Ala Asn Asn Lys Cys Leu Cys Gly Ser Pro Leu Pro
    210                 215                 220
Ala Cys Thr
225
```